US010253090B2

(12) United States Patent
Elnajjar et al.

(10) Patent No.: US 10,253,090 B2
(45) Date of Patent: Apr. 9, 2019

(54) HYDROLYZED COLLAGEN COMPOSITIONS AND METHODS OF MAKING THEREOF

(71) Applicant: AVICENNA NUTRACEUTICAL, LLC, Alpharetta, GA (US)

(72) Inventors: Ali Elnajjar, Atlanta, GA (US); Ali Mourad, Duluth, GA (US); Mark Ernst Brandt, Terre Haute, IN (US); Christopher Lippelt, Greenwood, IN (US)

(73) Assignee: Avicenna Nutraceutical, LLC, Alpharetta, GA (US)

( * ) Notice: Subject to any disclaimer, the term of this patent is extended or adjusted under 35 U.S.C. 154(b) by 0 days.

(21) Appl. No.: 15/569,240

(22) PCT Filed: Mar. 20, 2017

(86) PCT No.: PCT/US2017/023181
§ 371 (c)(1),
(2) Date: Oct. 25, 2017

(87) PCT Pub. No.: WO2017/165281
PCT Pub. Date: Sep. 28, 2017

(65) Prior Publication Data
US 2018/0319866 A1 Nov. 8, 2018

Related U.S. Application Data

(60) Provisional application No. 62/311,575, filed on Mar. 22, 2016.

(51) Int. Cl.
*C07K 14/78* (2006.01)
*C08L 89/06* (2006.01)

(52) U.S. Cl.
CPC .............. *C07K 14/78* (2013.01); *C08L 89/06* (2013.01)

(58) Field of Classification Search
None
See application file for complete search history.

(56) References Cited

U.S. PATENT DOCUMENTS

| | | | |
|---|---|---|---|
| 3,907,580 A | 9/1975 | Van Ham | |
| 4,032,464 A | 6/1977 | Mausner | |
| 4,130,555 A | 12/1978 | Ohtsuka | |
| 4,344,967 A | 8/1982 | Easton | |
| 4,485,037 A | 11/1984 | Curtis | |
| 4,784,986 A | 11/1988 | Usher | |
| 4,871,530 A | 10/1989 | Grollier | |
| 5,008,105 A | 4/1991 | Grollier | |
| 5,173,288 A | 12/1992 | Everhart | |
| 5,306,504 A | 4/1994 | Lorenz | |
| 5,425,937 A | 6/1995 | Uchiwa | |
| 5,840,848 A | 11/1998 | Sturrock | |
| 6,025,327 A | 2/2000 | Alkayali | |
| 6,090,915 A | 7/2000 | Herreid | |
| 6,255,279 B1 | 7/2001 | Christophers | |
| 6,323,319 B1 | 11/2001 | Alkayali | |
| 6,335,457 B1 | 1/2002 | Seguin | |
| 6,337,389 B1 | 1/2002 | Wolfinbarger | |
| 6,423,747 B1 | 7/2002 | Lanzendorfer | |
| 6,497,889 B2 | 12/2002 | Takekoshi | |
| 6,534,687 B2 | 3/2003 | Schultz | |
| 6,548,077 B1 | 4/2003 | Gunasekaran | |
| 6,649,178 B2 | 11/2003 | Mohammadi | |
| 6,669,932 B2 | 12/2003 | Imanaka | |
| 6,780,841 B2 | 8/2004 | Ishaq | |
| 6,838,440 B2 | 1/2005 | Stiles | |
| 6,844,424 B1 | 1/2005 | Mollard | |
| 6,916,910 B2 | 7/2005 | Wolfinbarger | |
| 7,083,820 B2 | 8/2006 | Schilling | |
| 7,091,180 B2 | 8/2006 | Ishaq | |
| 7,241,871 B2 | 7/2007 | Wolfinbarger | |
| 7,485,323 B2 | 2/2009 | Dolphin | |
| 7,495,076 B2 | 2/2009 | Gu | |
| 7,608,588 B2 | 10/2009 | Gu | |
| 7,671,041 B2 | 3/2010 | Vouland | |
| 7,781,158 B2 | 8/2010 | Yu et al. | |
| 7,799,348 B2 | 9/2010 | Ishaq | |
| 7,846,487 B2 | 12/2010 | Schilling | |
| 7,897,728 B2 | 3/2011 | Dolphin | |
| 8,066,977 B2 | 11/2011 | Shibuya | |
| 8,344,106 B1 | 1/2013 | Summers | |
| 8,414,872 B2 | 4/2013 | Resnick | |
| 8,425,949 B2 | 4/2013 | Ohishi | |
| 8,470,975 B2 | 6/2013 | Summers | |
| 8,518,422 B2 | 8/2013 | Monks | |
| 8,551,508 B2 | 10/2013 | Lee | |
| 8,551,509 B2 | 10/2013 | Aoki | |
| 8,563,045 B2 | 10/2013 | Ishaq | |
| 8,563,072 B2 | 10/2013 | Suvee | |
| 8,580,849 B2 | 11/2013 | Ishii | |
| 8,652,530 B1 | 2/2014 | Moore | |
| 8,748,499 B2 | 6/2014 | Lau | |
| 2002/0012640 A1 | 1/2002 | Mohammadi | |
| 2002/0009472 A1 | 4/2002 | Takekoshi | |
| 2003/0044456 A1 | 3/2003 | Ichie | |
| 2005/0249691 A1 | 10/2005 | Monks | |
| 2005/0287182 A1 | 12/2005 | Monks | |
| 2006/0194760 A1 | 8/2006 | Griesbach | |
| 2006/0257346 A1 | 11/2006 | Mohammadi | |
| 2007/0041925 A1 | 2/2007 | Picano | |
| 2007/0219128 A1 | 9/2007 | Chen et al. | |
| 2007/0231878 A1 | 10/2007 | Wu et al. | |

(Continued)

OTHER PUBLICATIONS

International Search Report and Written Opinin for PCT/US17/23181 dated Jun. 16, 2017.

*Primary Examiner* — Marcela M Cordero Garcia
(74) *Attorney, Agent, or Firm* — Gardner Groff Greenwald & Villanueva, PC

(57) ABSTRACT

Disclosed herein are hydrolyzed collagen compositions. The compositions are inexpensive to make and can be produced without the use of proteolytic enzymes, decolorizing agents, antibacterial and antifungal agents, and the like. Further, the compositions are substantially free of odors and are white to light yellow in color and are suitable to be used as dietary supplements. Also disclosed are methods for producing the compositions.

20 Claims, No Drawings

(56) References Cited

U.S. PATENT DOCUMENTS

| | | |
|---|---|---|
| 2008/0063674 A1 | 3/2008 | Vollhardt |
| 2008/0131389 A1 | 6/2008 | Shibuya |
| 2008/0206172 A1 | 8/2008 | Mohammadi |
| 2009/0081147 A1 | 3/2009 | Shibuya |
| 2009/0098214 A1 | 4/2009 | Nanbu |
| 2009/0312524 A1 | 12/2009 | Lauritzen |
| 2010/0055218 A1 | 3/2010 | Raederstorff |
| 2010/0056463 A1 | 3/2010 | Raederstorff |
| 2010/0068342 A1 | 3/2010 | Matsumoto |
| 2010/0273877 A1 | 10/2010 | Aoki |
| 2010/0303698 A1 | 12/2010 | Lau |
| 2010/0322887 A1 | 12/2010 | Aoki |
| 2011/0033606 A1 | 2/2011 | Ito |
| 2011/0034392 A1 | 2/2011 | Ishaq |
| 2011/0123579 A1 | 5/2011 | Mohammadi |
| 2011/0135699 A1 | 6/2011 | Dick |
| 2012/0064182 A1 | 3/2012 | Gohla |
| 2012/0128618 A1 | 5/2012 | Claas |
| 2012/0141387 A1 | 6/2012 | Msika |
| 2012/0157391 A1 | 6/2012 | Goto |
| 2012/0251473 A1 | 10/2012 | Knappe |
| 2013/0029914 A1 | 1/2013 | Ito |
| 2013/0116189 A1 | 5/2013 | Tanihara |
| 2013/0217748 A1 | 8/2013 | Sartingen |
| 2013/0252899 A1 | 9/2013 | Hausmanns |
| 2013/0310540 A1 | 11/2013 | Kato |
| 2013/0345168 A1 | 12/2013 | Kim |
| 2014/0023605 A1 | 1/2014 | Scheunemann |
| 2014/0080761 A1 | 3/2014 | Goto |
| 2014/0113861 A1 | 4/2014 | Ferrer |

HYDROLYZED COLLAGEN COMPOSITIONS AND METHODS OF MAKING THEREOF

CROSS REFERENCE TO RELATED APPLICATIONS

This application claims priority upon U.S. provisional application Ser. No. 62/311,575 filed Mar. 22, 2016. This application is hereby incorporated by reference in its entirety for all of its teachings.

BACKGROUND

Collagen preparations have been used in a variety of capacities, from gelling agents in food, to pharmaceuticals and health aids, to photography, cosmetic manufacturing, and adhesives. Within the health industry, collagen preparations have been used to enhance athletic performance by supplying essential amino acids and shortening recovery time after exercise, and have also been used as weight loss aids and digestive aids as well as to relieve pain, reduce inflammation, and improve joint function for patients with osteoarthritis and rheumatoid arthritis. Collagen preparations have been used as supplements to combat osteoporosis and improve the condition of fingernails and hair. In the cosmetic industry, meanwhile, collagen preparations are available as topical products for use on the skin to increase skin suppleness, reduce the appearance of wrinkles and fine lines, and to reduce the appearance of stretch marks.

Although the raw materials for extracting collagen are readily available as byproducts from other industries, such as the fishing and poultry processing industries, current methods for producing collagen are expensive and time-consuming Cartilage tissue must be separated from meat and bones and chopped. Hydrolysis of collagen often requires the sequential use of multiple enzymes, each of which likely performs best in a different set of reaction conditions (e.g., temperature, salt content, solution pH, etc.). Further, specialized digestive enzymes are expensive and the cost increases when multi-enzyme cocktails are used, especially on an industrial scale. Following hydrolysis, a number of purification steps are often required, including the use of decolorizing agents, antibacterial and antifungal agents, and the like. Product odor is also a consideration; collagen preparations with strong odors will be unsuitable especially for incorporation into cosmetic or food products.

It would thus be advantageous to have an enzyme-free process for producing hydrolyzed collagen preparations. It would further be advantageous if this process resulted in a product or products with a white or light yellow color and minimal to no odor. Still further, it would be advantageous if collagen preparations produced according to this process were able to supply essential minerals in addition to the amino acids and peptides naturally present in the preparations. The present invention addresses these needs.

SUMMARY

Disclosed herein are hydrolyzed collagen compositions. The compositions are inexpensive to make and can be produced without the use of proteolytic enzymes, decolorizing agents, antibacterial and antifungal agents, and the like. Further, the compositions are substantially free of odors and are white to light yellow in color and are suitable to be used as dietary supplements. Also disclosed are methods for producing the compositions.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an acid" includes mixtures of two or more such acids, and the like.

"Optional" or "optionally" means that the subsequently-described event or circumstance can or cannot occur, and that the description includes instances where the event or circumstance occurs and instances where it does not.

As used herein, "cartilage" refers to a type of connective tissue in animals. It is a flexible tissue that is somewhat more rigid than muscle and is found in various locations throughout the body including joints, the rib cage, the nose and ear, bronchial tubes, trachea, between the vertebra, and so forth. Cartilage tissue contains a large amount of extracellular matrix that is high in collagen and other proteoglycans. Chondrocytes are matrix-producing cells that have become trapped in the matrix.

"Collagen" is a structural protein found in connective tissue; it frequently takes the form of fibrils arranged in a triple helix. Fibrillar types of collagen include Types I, II, III, V, and XI. Type I collagen makes up a great deal of the organic part of bone as well as being found in skin, tendons, blood vessels, and organs, while type III collagen is commonly found near or with type I. On the other hand, cartilage is composed primarily of type II collagen. Other types of cartilage are less common and may be found in membranes, on cell surfaces, and associated with hair and placental structures.

As used herein, "hydrolysis" refers to the breaking of a chemical bond in a molecule via the molecule's reaction with water. Thus, a nucleic acid would be hydrolyzed into oligonucleotides and component nucleotides, a protein into peptides and amino acids, a polysaccharide into oligosaccharides and component sugars, and so forth. The degree of completion of hydrolysis is dependent upon reaction conditions. Hydrolysis can be accomplished in basic solution, in acidic solution, in a salt solution (usually when the salt is a weak acid or base), or using an enzyme.

"Hydrolyzed collagen" as used herein is collagen that has been subjected to a hydrolysis process. "Gelatin" is collagen that has been partially hydrolyzed and possesses specific properties such as solubility in hot water and a similar amino acid composition to the parent collagen.

The sternum, or breastbone, is a large bone to which the pectoral muscles are attached. In avians such as chickens, the sternum is positioned under the body and is enlarged in size for attachment of powerful flight muscles. Avian sterna are typically associated with a large proportion of cartilage that is rich in type II collagen.

As used herein, "neutralization" refers to the treatment of an acidic reaction solution with an approximately quantitative amount of a base. Neutralization with base can stop an acidic hydrolysis reaction, for example.

An "anti-bacterial agent" is any compound or composition or treatment that destroys bacteria. Alternatively, an anti-bacterial agent can suppress the growth of bacteria or can prevent bacteria from reproducing. Ultraviolet light, heat treatment, certain chemicals such as bleach or ethanol, and antibiotics are considered anti-bacterial.

As used herein, the term "about" is used to provide flexibility to a numerical range endpoint by providing that a given value may be "a little above" or "a little below" the endpoint without affecting the desired result.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the list solely based on their presentation in a common group without indications to the contrary.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference of each various individual and collective combination and permutation of these compounds may not be explicitly disclosed, each is specifically contemplated and described herein. For example, if an acid is disclosed and a number of different neutralizing bases are discussed, each and every combination and permutation of acid and base that is possible is specifically contemplated unless specifically indicated to the contrary. For example, if a class of molecules A, B, and C are disclosed, as well as a class of molecules D, E, and F, and an example of a combination A+D is disclosed, then even if each is not individually recited, each is individually and collectively contemplated. Thus, in this example, each of the combinations A+E, A+F, B+D, B+E, B+F, C+D, C+E, and C+F, are specifically contemplated and should be considered disclosed from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered disclosed from disclosure of A, B, and C; D, E, and F; and the example combination of A+D. This concept applies to all aspects of this disclosure including, but not limited to, steps in methods of making and using the disclosed compositions. Thus, if there exist a variety of additional steps that can be performed with any specific embodiment or combination of embodiments of the disclosed methods, each such combination is specifically contemplated and should be considered disclosed.

References in the specification and concluding claims to parts by weight of a particular element or component denote the weight relationship between the element or component and any other elements or components in the compound or composition for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Provided herein are compositions containing collagen as well as methods to produce the compositions. In one aspect, the collagen is hydrolyzed. In another aspect, the collagen is sourced from vertebrate cartilage. In a further aspect, the vertebrate is a fish, mammal, or avian. In a still further aspect, the vertebrate is a chicken and the cartilage is sternal cartilage, while the collagen is type II collagen.

In one aspect, provided herein is a method for producing hydrolyzed collagen, the method including the following steps:

(a) heating a chicken sternum in the presence of an aqueous acid at an elevated temperature for a time period to produce a first composition;
(b) filtering the first composition to remove the supernatant;
(c) neutralizing the acid present in the supernatant to produce a neutralized supernatant; and
(d) removing the water in the neutralized supernatant to produce the hydrolyzed collagen.

Each step of the process described herein is discussed in detail below.

In one aspect, prior to step (a), the chicken sternum is removed from the chicken skeleton. Here, all of the meat is removed from the chicken sternum or substantially all of the meat is removed (e.g., greater than 90%, greater than 95%, or greater than 99%).

In another aspect, the chicken sternum is treated with an anti-bacterial agent prior to step (a). Examples of anti-bacterial agents useful herein include, but are not limited to, ethanol, isopropanol, chlorine, bleach, a peroxide, a quaternary ammonium compound, or a combination thereof. In a further aspect, prior to step (a), the chicken sternum is boiled then the temperature is reduced prior to hydrolysis. In an alternative aspect, if the chicken sternum is processed immediately, an anti-bacterial agent is not required.

After the chicken sternum has been removed, it can be processed further prior to hydrolysis. For example, the chicken sternum can be chopped or pulverized to increase the surface area of the sternum.

After the chicken sternum has been removed, it is subjected to acid hydrolysis. The selection of the hydrolysis conditions in step (a) is important with respect to producing highly pure hydrolyzed collagen that has little to no odor or discoloration.

In one aspect, the acid is a strong acid. In a further aspect, the acid is selected from hydrochloric acid, hydroiodic acid, hydrobromic acid, perchloric acid, nitric acid, sulfuric acid, or a combination thereof. In one aspect, the acid is present in solution at a concentration of from 0.5 M to 4 M, or is about 0.5 M, about 1 M, about 1.5 M, about 2 M, about 2.5 M, about 3 M, about 3.5 M, or about 4 M, where any value can be a lower and upper endpoint of a range (e.g., 1 M to 3 M). In another aspect, a lower acid concentration will result in less base needed for neutralization. In some aspects, when the acid concentration was less than 1 M, little or no hydrolysis was observed at 12 hours.

The ratio of the amount of acid to the chicken sternum is important with respect to the purity of the final hydrolyzed collagen. In one aspect, the ratio of the chicken sternum per mole of acid is from 500 grams to 5,000 grams of chicken sternum per mole of acid, or is about 500, 525, 550, 575, 600, 625, 650, 675, 700, 725, 750, 1,000; 1,100; 1,200; 1,300; 1,400; 1,500; 2,000; 2,500; 3,000; 3,500; 4,000; 4,500, or 5,000 grams of chicken sternum per mole of acid, where any value can be a lower and upper endpoint of a range (e.g., 500 to 750). Thus, by varying the amount of the chicken sternum and concentration of the acid, it is possible to vary the ratios above. The Examples provide calculations for determining these ratios.

The hydrolysis step (a) is conducted at an elevated temperature. In one aspect, the elevated temperature is from 50° C. to boiling, or is about 50° C., about 55° C., about 60° C., about 65° C., about 70° C., about 75° C., about 80° C., about 90° C., about 95° C., or about 100° C., where any value can be a lower and upper endpoint of a range (e.g., 55° C. to 65° C.).

The duration of the hydrolysis step (a) is also important with respect to producing highly pure hydrolyzed collagen. In one aspect, the duration of hydrolysis is from 2 hours to 48 hours, or is about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 24 hours, or about 48 hours where any value can be a lower and upper endpoint of a range (e.g., 8 to 12 hours). In another aspect, the duration of hydrolysis is from 10 hours to 20 hours, 15 hours to 20 hours, 16 hours to 18 hours, or about 17 hours.

As discussed above, the conditions of the hydrolysis step are important with respect to producing highly pure hydrolyzed collagen. For example, hydrolysis slows when the reaction temperature drops below 50° C. Furthermore, longer heating times result in more highly-colored products. In one aspect, the chicken sternum is heated in the presence of hydrochloric acid at a temperature of from 58° C. to 62° C. for a time period of 16 to 18 hours. Further in this aspect, the chicken sternum can be present in a ratio of from 500 grams to 1,000 grams per mole of acid.

In another aspect, the hydrolysis reaction can be performed in open air, under vacuum, or under a nitrogen atmosphere. The hydrolysis step can be performed in a batch process or continuous process.

In one aspect, after hydrolysis step (a), the resulting mixture is optionally filtered to remove any insoluble materials. Standard filtration techniques can be used in this aspect.

After the hydrolysis step (a), a neutralization step is performed. In one aspect, the mixture produced after step (a) can be neutralized directly. In another aspect, if a filtration step is performed, the acid in the supernatant is neutralized with a base. The concentration and amount of base used in the neutralization step is generally in the amount to completely neutralize all of the acid present in the supernatant or substantially neutralize all of the acid (e.g., greater than 90%, greater than 95%, or greater than 99%).

In one aspect, the base is a strong base. In a further aspect, the strong base is sodium hydroxide, potassium hydroxide, calcium hydroxide, or a combination thereof. In an alternative aspect, the base is a weak base. Further in this aspect, the weak base is calcium carbonate, sodium carbonate, potassium carbonate, ammonia, sodium bicarbonate, or a combination thereof. In either of these aspects, the strong or weak base can be an alkali metal base or an alkaline earth metal base.

In a further aspect, the acid is neutralized with calcium hydroxide or calcium carbonate. In one aspect, calcium carbonate is preferred for neutralizing the substrate since calcium salts such as calcium chloride are left behind in the hydrolyzed collagen composition and these are safe for oral consumption by humans or other mammals. In a further aspect, the hydrolyzed collagen composition may provide some health benefits such as bone and joint support to a subject who consumes the composition. In a still further aspect, any calcium salts left behind after drying the hydrolyzed collagen composition provide a further health benefit such as bone support to a subject who consumes the composition. In an alternative aspect, drying a hydrolyzed collagen composition that has been neutralized by calcium carbonate requires less time and energy than drying a hydrolyzed collagen composition neutralized with another base, since calcium carbonate adsorbs less water than other bases.

After neutralization, the resulting mixture can be filtered to remove any insoluble materials and isolate the supernatant containing the hydrolyzed collagen. In the alternative, if a filtration step was performed after hydrolysis and prior to neutralization, no additional filtration is required of the neutralized supernatant. The water is removed from the neutralized supernatant to produce a dry solid or powder of the hydrolyzed collagen. Methods for removing the water from the supernatant include, but are not limited to, rotary evaporation, lyophilization, oven drying, or spray drying.

Also disclosed herein are hydrolyzed collagen products produced by the methods described herein. In one aspect, the hydrolyzed collagen has an average molecular weight of less than 10 kDa. In a further aspect, the hydrolyzed collagen has an average molecular weight of 1 kDa, 2 kDa, 3 kDa, 4 kDa, 5 kDa, 6 kDa, 7 kDa, 8 kDa, 9 kDa, or 10 kDa, or from about 3 kDa to about 5 kDa. In another aspect, the hydrolyzed collagen contains one or more calcium salts (e.g., $CaCl_2$) in an amount of less than 25% by weight of the hydrolyzed collagen, or about 5%, about 10%, about 15%, about 20%, or about 25% by weight of the hydrolyzed collagen where any value can be a lower and upper endpoint of a range (e.g., 10% to 25%). In one aspect, the average molecular weight of the hydrolyzed collagen can be altered by changing the hydrolysis reaction time.

In another aspect, the hydrolyzed collagen composition described herein contains hyaluronic acid in an amount of less than 10% by weight of the hydrolyzed collagen, or contains hyaluronic acid at about 1%, about 2%, about 3%, about 4%, about 5%, about 6%, about 7%, about 8%, or about 9% by weight of the hydrolyzed collagen where any value can be a lower and upper endpoint of a range (e.g., 2% to 9%). In another aspect, the hydrolyzed collagen composition contains less than 2% by weight, less than 1.5% by weight, or less than 1% by weight hyaluronic acid.

In another aspect, the hydrolyzed collagen composition described herein contains chondroitin sulfate in an amount of less than 10% by weight of the hydrolyzed collagen, or contains chondroitin sulfate at about 1%, about 2%, about 3%, about 4%, about 5%, about 6%, about 7%, about 8%, or about 9% by weight of the hydrolyzed collagen where any value can be a lower and upper endpoint of a range (e.g., 2% to 9%). In this aspect, the presence of chondroitin sulfate is derived from the chicken sternum and not an additional supplement. In another aspect, the hydrolyzed collagen composition contains less than 4% by weight chondroitin sulfate. In a further aspect, hydrolyzed collagen composition contains from 0.5% to 4% by weight chondroitin sulfate.

In a further aspect, the hydrolyzed collagen compositions described herein have little to no odor compared to other hydrolyzed collagen compositions. In another aspect, the hydrolyzed collagen compositions described herein have little or no color compared to other hydrolyzed collagen compositions and appear white or light yellow in color. In one aspect, color and odor are removed with the use of a decolorizing agent such as, for example, activated carbon or activated charcoal. In another aspect, charcoal or a decolorizing agent is not needed to remove color and odor from the hydrolyzed collagen composition.

In one aspect, the total protein level of the hydrolyzed collagen composition is greater than 80%, greater than 85%, or greater than 90%. In another aspect, the total collagen level of the hydrolyzed collagen composition is greater than 60%, greater than 65%, or greater than 70%.

EXAMPLES

The following examples are put forth so as to provide those of ordinary skill in the art with a complete disclosure and description of how the compounds, compositions, and methods described and claimed herein are made and evaluated. The examples are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions that can be used to optimize the product purity and yield obtained from the described process. Only reasonable and routine experimentation will be required to optimize such processes and conditions.

Ratio of Amount of Chicken Sternum per Mole of Acid

In Example 1, the amount of cartilage treated with the HCl was 5 g per 2 mL of acid. The following calculation was used to determine the amount of chicken sternum per mole of acid.

Moles of HCl in 2 mL of 2 M solution $$\frac{2 \text{ moles HCl}}{1 \text{ L}} \times \frac{1 \text{ L}}{1000 \text{ mL}} \times 2 \text{ mL} = 0.004 \text{ moles HCl}$$

Ratio of 5 g chicken sternum treated with 2 mL of 2 M HCl (i.e., 0.004 moles of HCl)

$$\frac{5 \text{ g chicken sternum}}{0.004 \text{ moles HCl}} = \frac{1{,}250 \text{ g chicken sternum}}{\text{mole HCl}}$$

Thus, when 5 g of chicken sternum is treated with 2 mL of 2 M HCl, this is equivalent to 1,250 g of chicken sternum treated with 1 mole of aqueous HCl.

Example 1: General Procedure

The following general procedure was used to prepare collagen hydrolysate from chicken sternal cartilage. Some parameters were varied during the course of optimization of conditions (see Example 2).

(1) Sternal cartilage was removed from chicken skeleton. Cartilage was either used immediately or stored in a volume of 70% ethanol sufficient to cover the biological material.

(2) 0.5 mL of 2M aqueous HCl per gram of cartilage was added.

(3) The mixture was placed in a reaction vessel at 60° C. and stirred vigorously for 12 hours.

(4) Optionally, the mixture was filtered. The filter was rinsed with ultrapure water to remove residual soluble material.

(5) The supernatant liquid was neutralized with either 0.25 mL of sodium hydroxide per mL of HCl originally used or, alternatively, with 0.11 g calcium carbonate per mL of HCl originally used. Neutralization with $CaCO_3$ results in the evolution of carbon dioxide gas.

(6) Water is removed from the neutralized supernatant. Lyophilization and/or spray drying were typically used. The final hydrolyzed collagen product is an off-white material having a "fluffy" appearance (Figs. 1 and 2).

Example 2: Experimental Permutations

Various parameters in the procedure of Example 1 were altered in order to optimize product yield. Results from several example procedures are presented in Table 1. Hydrolysis was evaluated using denaturing (SDS) polyacrylamide gel electrophoresis.

TABLE 1

Experimental Permutations

| Sample ID | Acid and Conc. | Cartilage (g)/Acid Ratio (mL) | Water Temp. (° C.) | Hydrolysis Time (hours) | Vacuum[f] | Base[g] | Evidence of Hydrolysis[h] |
|---|---|---|---|---|---|---|---|
| 10 | 2M HCl | | 100 | 5 | | | No |
| 11 | 2M HCl | | 90 | 5 | | | No |
| 12.1[a] | 2M HCl | | 50 | 2 | yes | | Yes |
| 12.2[a] | 2M HCl | | 60 | 2 | yes | | Yes |
| 12.3[a] | 2M HCl | | 80 | 2 | yes | | Yes |
| 13.1[a] | 2M HCl | | 60 | 4.5 | yes | | Yes |
| 13.2[a] | 2M HCl | | 70 | 4.5 | yes | | Yes |
| 13.3[a] | 2M HCl | | 80 | 4.5 | yes | | inconclusive |
| 14 | 2M HCl | | 90 | 8 | | | No |
| 14.S[b] | 2M HCl | | 90 | 8 | | | Yes |
| 15 | None | | 80 | 48 | | | unhydrolyzed |
| 16 | 2M HCl | | 50 | 24 | | | not tested |
| 17 | 2M HCl | 1:1 | 55-60 | 4.5 | yes | NaOH | No |
| 18 | 2M HCl | 1:1 | 50 | 96 | no | NaOH | |
| 21 | 2M HCl | 1:1 | 60 | 4.5 | no | NaOH | |
| 22.1[c] | 2M HCl | 5:2 | 60-65 | 10 | yes | NaOH | |
| 22.2[c] | 2M HCl | 5:2 | 55-60 | 10 | yes | NaOH | |
| 23 | 2M HCl | 5:2 | 60 | 10 | no | NaOH | |
| 24 | 2M HCl | 5:2 | 60 | 17 | no | CaCO$_3$ | |
| 24.F[d] | 2M HCl | 5:2 | 60 | 17 | no | CaCO$_3$ | |
| 24.I[e] | 2M HCl | 5:2 | 60 | 17 | no | CaCO$_3$ | |
| 25 | pepsin | 3% w/w | 35 | >60 days | no | | |
| 26 | 2M HCl | 7:3 | 60 | 18 | no | CaCO$_3$ | |

[a]Three replicates performed under similar set of conditions.
[b]Solids from filtering were analyzed.
[c]Two replicates performed under similar set of conditions.
[d]Unfiltered product analyzed.
[e]Filtrate analyzed.
[f]Hydrolysis reaction carried out under vacuum.
[g]Base added to neutralize acid at the completion of hydrolysis reaction.
[h]Appearance of bands in the SDS-PAGE gel that had migrated outside the sample wells was considered positive evidence of hydrolysis. In some cases, hydrolysis may have generated small peptides that ran off the end of the gel or were too small to stain.

Example 3: Characterization of Products

Products were subjected to HPLC analysis, method ALC190A, performed by Advanced Botanical Consulting & Testing, Inc. (Tustin, Calif.). This method detects and quantifies amino acids in bound form, after protein hydrolysis. Results from an example product are presented in Table 2.

TABLE 2

Amino Acid Analysis

| Amino Acid | % of Composition |
|---|---|
| Histidine | 0.49 |
| Arginine | 3.98 |
| Glutamine | 0.12 |
| Glycine | 10.37 |
| Serine | 9.31 |
| Glutamic acid | 8.92 |
| Aspartic acid | 8.87 |
| Proline | 6.87 |
| Threonine | 5.88 |
| Alanine | 0.00 |
| Tyrosine | 9.67 |
| Methionine | 1.06 |
| Lysine | 3.38 |
| Valine | 0.00 |
| Leucine | 4.41 |
| Isoleucine | 8.60 |
| Phenylalanine | 0.00 |
| Taurine | 4.25 |
| Total Amino Acids (calculated) | 86.16 |

In another experiment, hydrolysis was performed using the protocol in Example 1 with the exception that hydrolysis was conducted at 60° C. for 17 hours using 1 M HCl (ratio of 5 g cartilage per 2 mL of 1 M HCl). The amino acid content of the resulting hydrolysate is provided in Table 3 (two samples).

TABLE 3

Amino Acid Analysis

| Amino Acid | % of Composition | |
|---|---|---|
| Alanine | 4.51 | 7.11 |
| Arginine | 4.66 | 5.35 |
| Aspartic acid | 4.52 | 7.58 |
| Cystine | 0.41 | 0.60 |
| Glutamic acid | 8.19 | 12.36 |
| Glycine | 10.46 | 13.92 |
| Histidine | 1.21 | 1.55 |
| Isoleucine | 1.61 | 2.49 |
| Leucine | 3.29 | 4.18 |
| Lysine | 2.55 | 4.66 |
| Methionine | 1.00 | 1.30 |
| Phenylalanine | 1.86 | 1.90 |
| Proline | 6.04 | 8.51 |
| Serine | 2.00 | 3.30 |
| Threonine | 4.41 | 3.38 |
| Tryptophan | 0.29 | 0.34 |
| Tyrosine | 0.64 | 1.20 |
| Valine | 2.46 | 3.44 |

Throughout this publication, various publications are referenced. The disclosures of these publications in their entireties are hereby incorporated by reference into this application in order to more fully describe the methods, compositions, and compounds herein.

Various modifications and variations can be made to the methods, compositions, and compounds described herein. Other aspects of the methods, compositions, and compounds will be apparent from consideration of the specification and practice of the methods, compositions, and compounds disclosed herein. It is intended that the specification and examples be considered as exemplary.

What is claimed:

1. A method for producing hydrolyzed collagen, the method comprising
    (a) heating a chicken sternum in the presence of an aqueous acid at a temperature of from 55° C. to 100° C. for 8 to 48 hours, wherein the ratio of chicken sternum per mole of acid is from 250 g chicken sternum/mole of acid to 5,000 g chicken sternum/mole of acid to produce a first composition;
    (b) optionally filtering the first composition to remove the supernatant;
    (c) neutralizing the acid present in the supernatant to produce a neutralized supernatant; and
    (d) removing the water in the neutralized supernatant to produce the hydrolyzed collagen
    wherein the process does not use an enzyme.

2. The method of claim 1, wherein chicken sternum is removed from the chicken skeleton prior to step (a).

3. The method of claim 1, wherein chicken sternum is treated with an anti-bacterial agent prior to step (a).

4. The method of claim 1, wherein the chicken sternum is heated in the presence of an aqueous acid at a temperature of from 58° C. to 62° C. for 16 to 18 hours.

5. The method of claim 1, wherein the acid comprises hydrochloric acid.

6. The method of claim 1, wherein the ratio of chicken sternum per mole of acid is from 500 g chicken sternum/mole of acid to 2,000 g chicken sternum/mole of acid.

7. The method of claim 1, wherein the ratio of chicken sternum per mole of acid is from 500 g chicken sternum/mole of acid to 1,000 g chicken sternum/mole of acid.

8. The method of claim 1, wherein the supernatant is neutralized with an alkali metal base or an alkaline earth metal base.

9. The method of claim 1, wherein the supernatant is neutralized with sodium hydroxide or sodium carbonate.

10. The method of claim 1, wherein the supernatant is neutralized with calcium hydroxide or calcium carbonate.

11. The method of claim 1, wherein the water in step (d) is removed by lyophilization or spray drying.

12. The method of claim 1, wherein the chicken sternum is heated in the presence of aqueous hydrochloric acid at a temperature of from 58° C. to 62° C. for 16 to 18 hours, wherein the ratio of chicken sternum per mole of acid is from 500 g chicken sternum/mole of acid to 1,000 g chicken sternum/mole of acid.

13. The method of claim 12, wherein the supernatant is neutralized with calcium hydroxide or calcium carbonate.

14. Hydrolyzed collagen produced by the method of claim 1.

15. The hydrolyzed collagen of claim 14, wherein the hydrolyzed collagen has an average molecular weight of less than 10 kDa.

16. The hydrolyzed collagen of claim 14, wherein the hydrolyzed collagen comprises one or more calcium salts in the amount of less than 25% by weight of the hydrolyzed collagen.

17. The hydrolyzed collagen of claim 14, wherein the hydrolyzed collagen comprises hyaluronic acid in the amount of less than 2% by weight of the hydrolyzed collagen.

18. The hydrolyzed collagen of claim 14, wherein the hydrolyzed collagen comprises chondroitin sulfate in the amount of less than 4% by weight of the hydrolyzed collagen.

19. The method of claim 1, wherein in step (a) the chicken sternum is heated in the presence of an aqueous acid at a temperature of from 55° C. to 75° C. for 8 to 20 hours.

20. The hydrolyzed collagen of claim 14, wherein the hydrolyzed collagen has a molecular weight of from 1 kDa to 5 kDa.

* * * * *